United States Patent
Biyani (10) Patent No.: US 8,394,124 B2
(45) Date of Patent: Mar. 12, 2013

(54) UNIDIRECTIONAL ROTATORY PEDICLE SCREW AND SPINAL DEFORMITY CORRECTION DEVICE FOR CORRECTION OF SPINAL DEFORMITY IN GROWING CHILDREN

(75) Inventor: Ashok Biyani, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 146 days.

(21) Appl. No.: 12/818,258

(22) Filed: Jun. 18, 2010

(65) Prior Publication Data
US 2010/0324600 A1    Dec. 23, 2010

Related U.S. Application Data

(60) Provisional application No. 61/218,204, filed on Jun. 18, 2009.

(51) Int. Cl.
*A61B 17/70* (2006.01)
(52) U.S. Cl. .................................... 606/246; 606/300
(58) Field of Classification Search ............. 606/246, 606/250–264, 300–321, 279
See application file for complete search history.

(56) References Cited

U.S. PATENT DOCUMENTS

| | | | |
|---|---|---|---|
| 5,672,175 A | 9/1997 | Martin | |
| 5,797,910 A | 8/1998 | Martin | |
| 2007/0255407 A1* | 11/2007 | Castleman et al. | 623/17.11 |
| 2009/0024165 A1* | 1/2009 | Ferree | 606/246 |
| 2009/0182343 A1* | 7/2009 | Trudeau et al. | 606/102 |

* cited by examiner

*Primary Examiner* — Eduardo C Robert
*Assistant Examiner* — Christina Negrellirodriguez
(74) *Attorney, Agent, or Firm* — MacMillan, Sobanski & Todd, LLC (57) ABSTRACT

A scoliosis correction device includes a first fixed anchor that is adapted to be secured to a vertebra of a spine and a second fixed anchor that is adapted to be secured to a vertebra of a spine. A rotatory anchor includes a head portion, a shank portion that extends from the head portion and is adapted to be secured to a vertebra of a spine, and a sprocket that is supported on the head portion for rotational movement relative thereto. A cable extends from the first fixed anchor to the rotatory pedicle screw to the second fixed anchor. The rotatory anchor may be configured to allow unidirectional movement of the sprocket relative to the head portion. A rigid member may extend between the fixed anchor and an intermediate anchor.

19 Claims, 11 Drawing Sheets

UNIDIRECTIONAL ROTATORY PEDICLE SCREW AND SPINAL DEFORMITY CORRECTION DEVICE FOR CORRECTION OF SPINAL DEFORMITY IN GROWING CHILDREN

STATEMENTS REGARDING FEDERALLY SPONSORED RESEARCH OR DEVELOPMENT AND CROSS-REFERENCE TO RELATED APPLICATIONS

This invention was not made with any government support. This application claims the benefit of United States Provisional Application No. 61/218,204 filed Jun. 18, 2009, the disclosure of which is incorporated herein by reference.

BACKGROUND OF THE INVENTION

This invention relates in general to the field of orthopedic spinal surgery. In particular, this invention relates to an improved device for correcting a spinal deformity such as scoliosis and to an improved unidirectional rotatory pedicle screw that can be used in such a spinal deformity correcting device. This invention is particularly well suited for correcting spinal deformities in growing children and adolescents.

Scoliosis is a common spinal deformity that frequently occurs in growing children and adolescents. The majority of patients who develop scoliosis do not have any underlying skeletal disorder at birth, but develop spinal deformity during adolescence. Since there is no defined and obvious cause for development of scoliosis in this age group, it is usually called idiopathic scoliosis. Most patients with adolescent idiopathic or juvenile scoliosis are treated with conventional bracing until maturity or until the undesired curve deteriorates to such a significant degree that surgical correction is warranted. Several external, developmental, and radiological markers (such as family history, age at menarche, Risser sign, Tanner staging, severity of curve at presentation, documented progression, and chronologic age) are utilized to predict the severity and potential for progression of a curve. Oftentimes, it becomes difficult to accurately predict if a scoliosis deformity will become worse over time. Therefore, patients with curves of over twenty-five degrees and having the associated risk factors are typically braced until skeletal maturity.

Several genetic markers are being developed that have the potential to accurately predict which patients will eventually develop a significant deformity that would necessitate surgery. Those patients who are genetically not predisposed to progression of a mild scoliosis may simply be observed without expensive and cumbersome bracing. However, those patients who are genetically predisposed to significant worsening before skeletal maturity may benefit from preemptive surgery at a time when the curve is still small. Early surgery may be advantageous in children in whom genetic testing results are positive for future worsening of scoliosis deformity. Smaller curves would be amenable to improved correction and would mitigate further progression of spinal and rib deformity. Other advantages of such an approach would include less surgical trauma from minimally invasive surgery, shorter hospital stay, less bleeding and scarring, improved correction and an ability to modulate growth with a fusionless surgical correction of deformity. Subsequent removal of hardware and ability to maintain mobility of the scoliotic segment would also be significant benefits.

Most current methods of treatment include surgical correction of curves over forty-five degrees to fifty degrees with segmental instrumentation and fusion. Occasionally, some patients develop scoliosis in their pre-teen years or may have congenital scoliosis. Such spinal deformities are occasionally temporarily stabilized by internal growing rod construct. Typically, growth may be modulated by stapling or other tether mechanisms from the anterior approach utilizing thoracoscopic techniques. However, bilateral rods or cables or a hybrid technique combining rods and cables are more commonly performed for improved correction of the deformity.

Most current posterior instrumentation systems include several anchors that are strategically placed on both sides of the spinal curve. Then, the concave side is typically elongated and convex size rod or cable is compressed. Frequent surgical procedures are necessary to alter the construct to accommodate spinal growth and to correct any spinal deformity that may have developed since previous surgery. It would, therefore, be advantageous to have a minimally invasive spinal fixation system that addresses above-mentioned concerns associated with some of the current methods of treatment of adolescent idiopathic scoliosis.

SUMMARY OF THE INVENTION

This invention relates to an improved device for correcting a spinal deformity such as scoliosis and to an improved unidirectional rotatory pedicle screw that can be used in such a spinal deformity correcting device. This invention is particularly well suited for correcting spinal deformities in growing children and adolescents.

The disclosed invention combines a hybrid rod-cable that loops around rotatory pedicle screws anchored to the proximal most vertebrae included within the spinal deformity. The anchors placed on the superior aspect of the curve include rotatory pedicle screws that are unidirectional. Most patients have a right thoracic curve, which means that left side is typically shorter than right. In this setting, the proximal anchors would facilitate movement of the cable from left to right. In a case where a left sided curve needs to be corrected, a mirror image of the rotatory pedicle screws that permit counterclockwise movement only may be utilized.

In the disclosed invention, growth and elongation of the spinal column on convex side of the curve is exploited to correct growth inequality between the two sides. The construct has four different components, namely fixed, intermediate, and rotatory anchors and a unitized longitudinal member for anchoring on both sides of the spine. The fixed anchors are typically fixed the convex side, but may be fixed on both sides and are located at the bottom of the curve. These fixed anchors secure the longitudinal member in a non-slidable manner. The longitudinal member may be in the form of a cable or a rod at this level. Intermediate anchors may be placed on intermediate segments of the curve. These intermediate anchors are configured to facilitate surgical correction of the deformity during initial installation. These intermediate anchors secure the longitudinal member in a slidable manner such that they facilitate unidirectional elongation on the concave side. The rotatory anchors consist of unidirectional rotatory pedicle screws that facilitate attachment of the cable that is guided from concave side to the convex side of the deformity. These unidirectional pedicle screws incorporate a sprocket with a one way rolling mechanism, essentially acting as an overrunning clutch. The overrunning clutch allow free movement in one direction and prevents rotation in the other direction.

The longitudinal member is a unitary device that loops around the unidirectional screws that are placed at the proximal end of the construct. In one embodiment of the invention, the longitudinal member may be elongatable on the concave side but not on convex side of the spinal deformity. On the concave side, the longitudinal member consists of a cylindrical hollow member that houses a cable in its interior. The intermediate segment of the longitudinal member is configured to loop around the rotatory pedicle screws. It has a chain-cable type configuration such that it engages the projections on the rotatory pedicle screws. The longitudinal member is slidably fixed to the intermediate vertebral segments on the convex side but does not elongate. The distalmost portions at both ends of the longitudinal member may be in the form of a cable or a rod and is secured non-slidably to the distal-most pedicle screws.

As the spinal column grows more rapidly on the convex side, differential growth exerts a pull on the proximal most rotatable anchor on the convex side that, in turn, transmits the forces to the rotatable member on the concave side. The latter action leads to transfer of elongation forces on the longitudinal member between the anchors on the concave side. As a result, the cable that is housed within the cylindrical longitudinal rod is elongated. The rotatory pedicle screws facilitate unidirectional forces only and the cable, once elongated, is not allowed to retract back to its original length.

In order to prevent soft tissue ingrowth and prevent cables from getting entangled in the soft tissue, a silastic covering may be placed around the cables. The silastic forms a smooth well lubricated tunnel within six to eight weeks. Silastic has an extended safety record and is often used in hand surgery during two-stage tendon transfer procedures. Other biocompatible non-adherent coverings may also be utilized. In this manner, a smooth gliding excursion of the cable will be maintained.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figure 1:
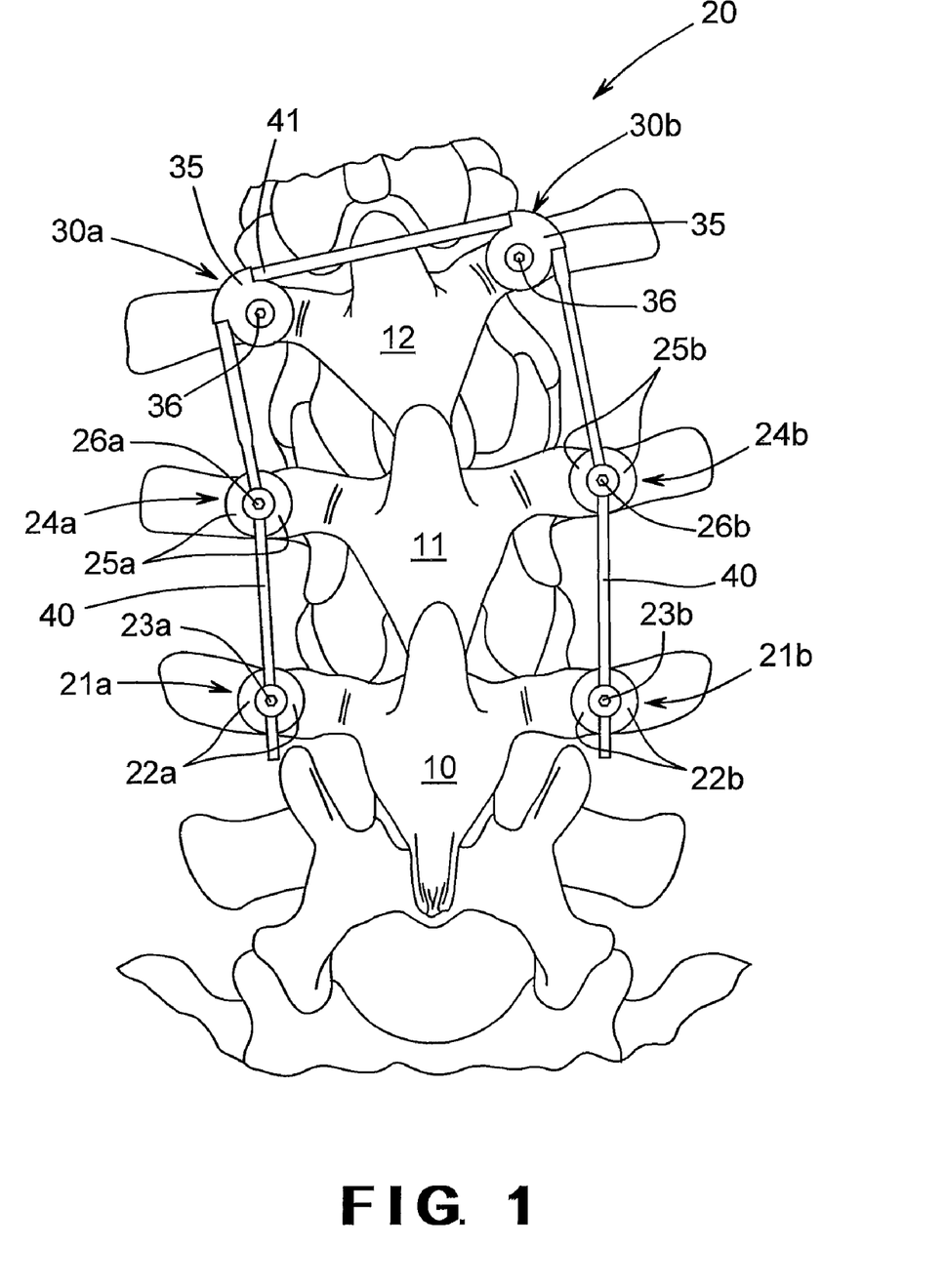
FIG. 1 is a schematic elevational view of three vertebrae of a portion of a spine having a first embodiment of a scoliosis correcting device in accordance with this invention secured thereto, wherein the vertebrae of the spine are shown in an initial scoliotic orientation.
Figure 2:
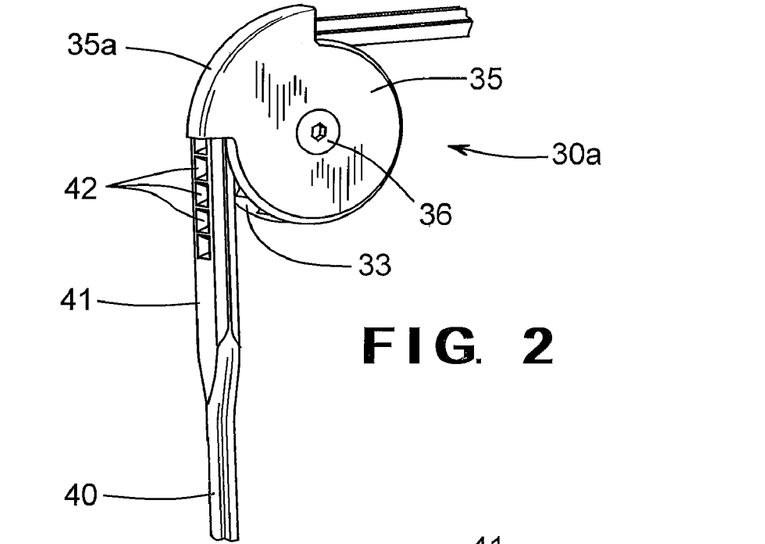
FIG. 2 is an enlarged perspective view of a unidirectional rotatory pedicle screw and a portion of a cable that are used in the scoliosis correcting device illustrated in FIG. 1.
Figure 3:
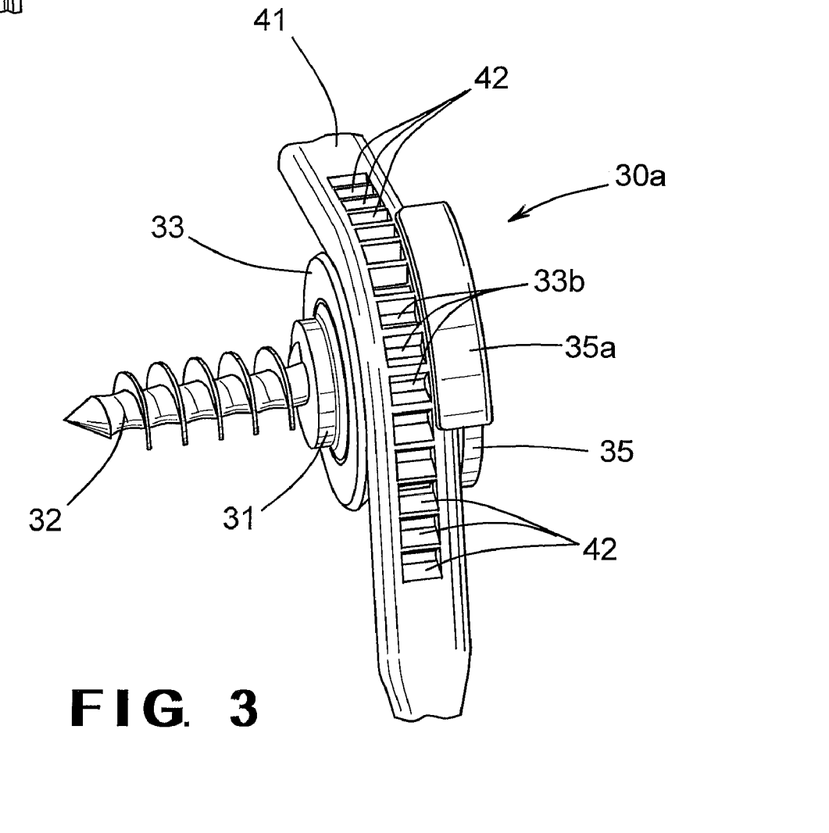
FIG. 3 is a further enlarged perspective view from a different angle of the unidirectional rotatory pedicle screw and the portion of the cable illustrated in FIG. 2.
Figure 4:
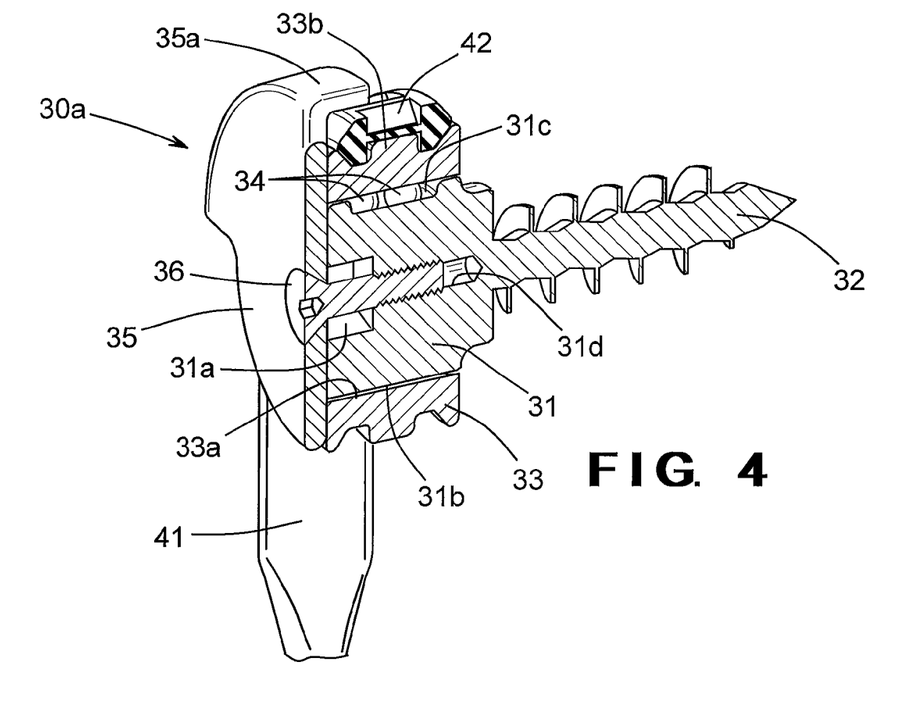
FIG. 4 is a perspective sectional view taken along a vertical plane of the unidirectional rotatory pedicle screw and the portion of the cable illustrated in FIGS. 2 and 3.
Figure 5:
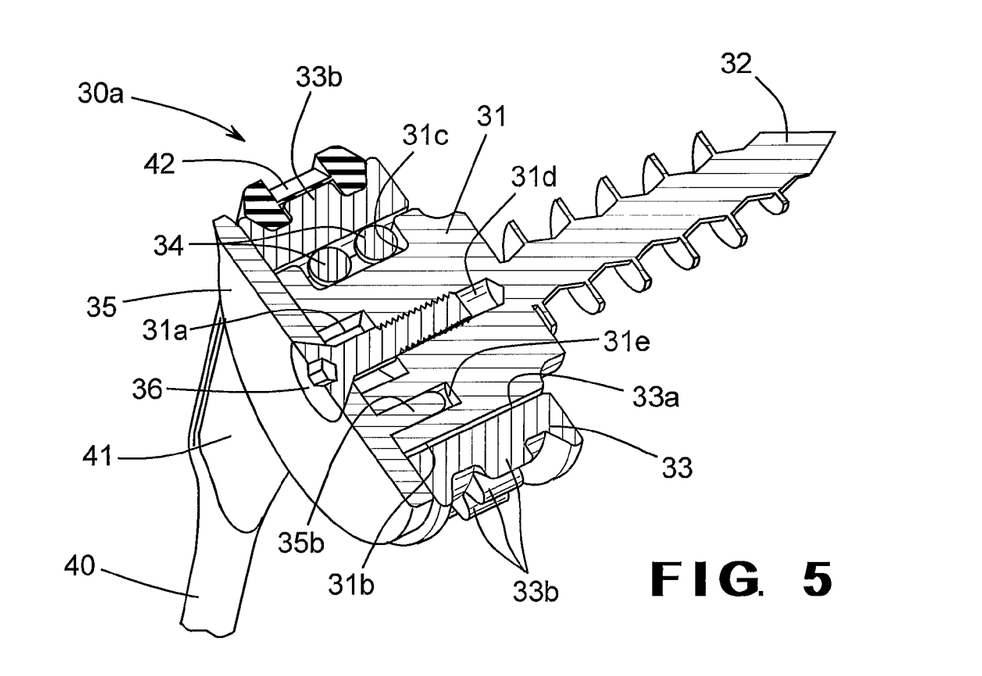
FIG. 5 is a perspective sectional view taken along a horizontal plane of the unidirectional rotatory pedicle screw and the portion of the cable illustrated in FIGS. 2 through 4.
Figures 6, 7:
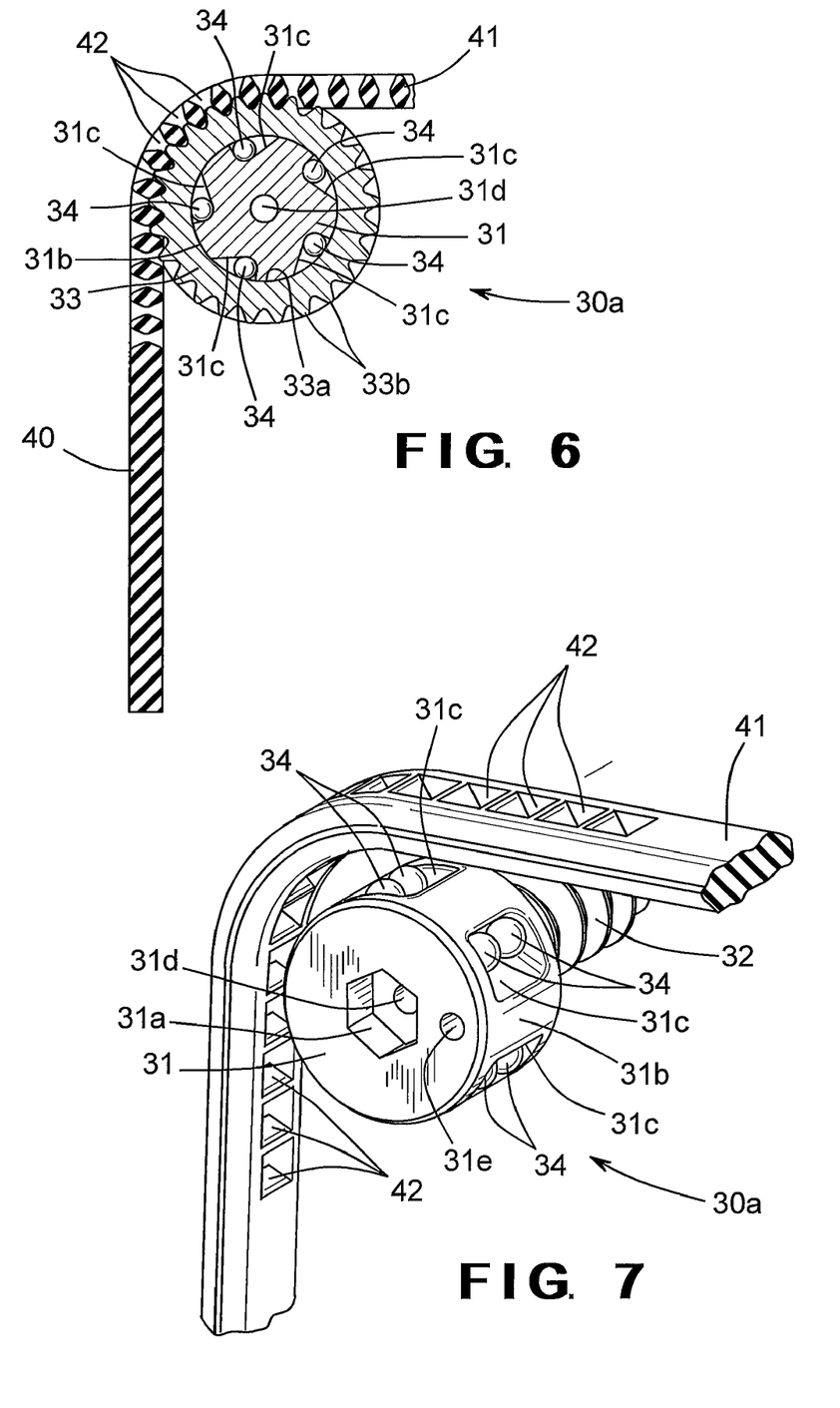
FIG. 6 is a sectional elevational view of the unidirectional rotatory pedicle screw and the portion of the cable illustrated in FIGS. 2 through 5.
FIG. 7 is an enlarged perspective view of portions of the unidirectional rotatory pedicle screw and the cable illustrated in FIGS. 2 through 6.

Referring now to the drawings, there is illustrated in FIG. 1 three vertebrae 10, 11, and 12 of a portion of a spine. The illustrated vertebrae 10, 11, and 12 may be located in any region of the spine, but typically are located in the thoracic or lumbar regions. The three vertebrae 10, 11, and 12 are shown in a curved orientation relative to one another, wherein the left sides of the vertebrae 10, 11, and 12 are spaced apart from one another by shorter distances than the right sides thereof. As a result, the left side of the illustrated portion of the spine presents a concave shape, while the right side of the illustrated portion of the spine presents a convex shape. Such a condition is referred to as scoliosis, which is an abnormal curvature of the spine when viewed from the front or rear. Typically, scoliosis involves a relatively large number of vertebrae (i.e., more than three) in the spine. However, for the sake of simplicity and to facilitate the understanding of this invention, only three vertebrae 10, 11, and 12 of the spine will be described and illustrated herein. Nonetheless, it will be appreciated that this invention may be used to correct a scoliotic condition involving a greater or lesser number of vertebrae in any desired region of the spine.

A first embodiment of a device, indicated generally at 20, is provided for correcting the scoliotic condition illustrated in FIG. 1. The first embodiment of the scoliosis correcting device 20 includes a pair of fixed anchors, indicated generally at 21a and 21b. In the first embodiment illustrated in FIG. 1, each of the fixed anchors 21a and 21b is secured to the first vertebra 10, which is located at or near a first end of the scoliotic portion of the spine (the lower end in the illustrated embodiment). However, the fixed anchors 21a and 21b may be secured to a different vertebra or to different vertebrae of the spine if desired.

Each of the fixed anchors 21a and 21b is conventional in the art and may, for example, be embodied as a conventional pedicle screw. A typical pedicle screw 21a and 21b includes a head portion having an externally threaded shank portion (not shown) extending therefrom. The head portion of the pedicle screw 21a and 21b may be fixed in position relative to the threaded shank portion (typically referred to as a mono-axial arrangement) or may be pivotable or otherwise movable relative to the threaded shank portion (typically referred to as a poly-axial arrangement). In either instance, the head portion of the pedicle screw 21a and 21b is preferably provided with a generally U-shaped yoke 22a and 22b for a purpose that will be explained below. The generally U-shaped yokes 22a and 22b are preferably each provided with a retaining structure (such as an internally threaded surface), that receives a retainer 23a and 23b (such as an externally threaded screw), again for a purpose that will be explained below. The head portions of the pedicle screw 21a and 21b may also be provided with conventional structures (not shown) that facilitate the use of a tool (not shown) such as a screwdriver to effect rotation thereof. The threaded shank portion of the pedicle screws 21a and 21b are adapted to be threaded by such rotation into engagement with a portion of the associated vertebra 10 in a manner that is well known in the art. The fixed anchors 21a and 21b may be formed from any desired material, such as titanium, stainless steel, cobalt-chrome, or any other suitable biomaterial.

The first embodiment of the scoliosis correcting device 20 also includes one or more intermediate anchors, indicated generally at 24a and 24b. In the first embodiment illustrated in FIG. 1, two of such intermediate anchors 24a and 24b are secured to the second vertebra 11, which is located within an intermediate portion of the scoliotic portion of the spine. However, as will be explained in greater detail below, the intermediate anchors 24a and 24b may be secured to a different vertebra or to different vertebrae of the spine if desired. Alternatively, either or both of the intermediate anchors 24a and 24b may be omitted entirely from the scoliosis correcting device 20 if desired. The intermediate anchors 24a and 24b can have the same general structure as the fixed anchors 21a and 21b described above, including respective generally U-shaped yokes 25a and 25b and retainers 26a and 26b. However, as will be described in detail below, the purpose and manner of operation of the intermediate anchors 24a and 24b are different from the purpose and manner of operation of the fixed anchors 21a and 21b. The intermediate anchors 24a and 24b may be formed from any desired material, such as titanium, stainless steel, cobalt-chrome, or any other suitable biomaterial.

The first embodiment of the scoliosis correcting device 20 further includes a pair of rotatory anchors, indicated generally at 30a and 30b. In the embodiment illustrated in FIG. 1, two of such rotatory anchors 30a and 30b are secured to the third vertebra 12, which is located at or near a second end of the scoliotic portion of the spine (the upper end in the illustrated embodiment). However, the rotatory anchors 30a and 30b may be secured to a different vertebra or to different vertebrae of the spine if desired.

The structure of one of the rotatory anchors 30a is illustrated in detail in FIGS. 2 through 7. As shown therein, the rotatory anchor 30a includes a head portion 31 having an externally threaded shank portion 32 extending therefrom. The head portion 31 includes an axially facing end surface having a drive structure 31a provided therein. The illustrated drive structure 31a is shown as hexagonal in shape and is adapted to cooperate with a conventional tool (such as a conventional hex-head screwdriver) to effect rotation of the rotatory anchor 30a relative to the associated third vertebra 12. However, the drive structure 31a may have any other desired shape or design. Thus, in a manner that is well known in the art, the rotatory anchor 30a can be secured to the third vertebra 12 of the scoliotic portion of the spine.

The head portion 31 of the rotatory anchor 30a also has an outer circumferential surface 31b. A sprocket 33 is supported on the head portion 31 of the rotatory anchor 30a for movement relative thereto. The sprocket 33 may be embodied having any desired shape or combination of shapes. In the illustrated embodiment, the sprocket 33 is annular in shape and has an inner circumferential surface 33a that is disposed concentrically about the outer circumferential surface 31b of the rotatory anchor 30a. Thus, the sprocket 33 is supported on the head portion 31 of the rotatory anchor 30a for rotational movement relative thereto. The illustrated sprocket 33 has a plurality of radially outwardly extending teeth 33b provided on an outer circumferential surface thereof. The purpose for these radially outwardly extending teeth 33b will be explained below.

It is desirable (but not required) that the sprocket 33 be supported on the head portion 31 of the rotatory anchor 30a for unidirectional rotational movement relative thereto, i.e., for movement relative to the head portion 31 in one rotational direction but not in the opposite rotational direction. To accomplish this, the head portion 31 and the sprocket 33 of the rotatory anchor 30a may be provided with an overrunning clutch or similar unidirectional rotational mechanism. In the illustrated embodiment, this unidirectional rotational mechanism includes a plurality of recesses 31c provided in the outer circumferential surface 31b of the rotatory anchor 30a. The illustrated outer circumferential surface 31b of the rotatory anchor 30a has five recesses 31c provided equidistantly therein. However, it will be appreciated that any desired number of such recesses 31c may be provided in the outer circumferential surface 31b of the rotatory anchor 30a. Within each of such recesses 31c, one or more ball bearings 34 are disposed. In the illustrated embodiment, two of such ball bearings 34 are provided within each of the recesses 31c provided in the outer circumferential surface 31b of the rotatory anchor 30a. However, it will be appreciated that any desired number of such ball bearings 34 (or other structures, for that matter) may be provided in such recesses 31c. The recesses 31c are shaped in such a manner that ball bearings 34 allow the sprocket 33 to rotate in a first rotational direction relative to the head portion 31 (clockwise when viewing FIG. 6) but prevent the sprocket 33 from rotating in a second rotational direction relative to the head portion 31 (counterclockwise when viewing FIG. 6). It will be appreciated that any desired structure may be provided for accomplishing this unidirectional rotational movement. The purpose for providing this unidirectional rotational movement will be explained below.

A cover 35 is secured to the axially facing end surface of the head portion 31 of the rotatory anchor 30a. In the illustrated embodiment, the cover 35 is secured to the axially facing end surface of the head portion 31 by a threaded fastener 36 that cooperates with a threaded bore 31d that extends co-axially from the drive structure 31a described above. The illustrated cover 35 has an optional flange portion 35a that extends axially about a portion of the sprocket 33. The purpose for this flange portion will be explained below. The cover 35 and the flange portion 35a can be maintained in a desired orientation relative to the head portion 31 of the rotatory anchor 30a (and, therefore, the sprocket 33) by means of a locating pin 35b that extends axially from the cover 35 into cooperation with a locating bore 31e provided in the head portion 31. Thus, when the cover 35 is secured to the axially facing end surface of the head portion 31 by the threaded fastener 36, it is positively maintained in a desired orientation relative thereto. The rotary anchors 30a may be formed from any desired material, such as titanium, stainless steel, cobalt-chrome, or any other suitable biomaterial.

Referring back to FIG. 1, it can be seen that a cable 40 extends throughout the fixed anchors 21a and 21b and the rotary anchors 30a and 30b of the scoliosis correcting device 20. The cable 40 is adapted to be connected to each of the fixed anchors 21a and 21b so as to be immovable relative thereto. In the illustrated embodiment, the cable 40 extends through each of the generally U-shaped yokes 22a and 22b provided on the head portions of the pedicle screws 21a and 21b. The associated retainers 23a and 23b provided within each of the generally U-shaped yokes 22a and 22b are fully tightened so as to frictionally engage the portions of the cable 40 extending therethrough. However, the cable 40 can be immovably connected to each of the fixed anchors 21a and 21b in any desired manner or combination of manners.

Also, the cable 40 is adapted to be connected to each of the intermediate anchors 24a and 24b so as to be movable relative thereto. In the illustrated embodiment, the cable 40 extends through each of the generally U-shaped yokes 25a and 25b provided on the head portions of the pedicle screws 24a and 24b. The associated retainers 26a and 26b provided within each of the generally U-shaped yokes 25a and 25b are partially tightened so as to retain the portions of the cable 40 extending therethrough but not to frictionally engage such portions of the cable 40, thereby allowing sliding movement of the cable 40 through each of the intermediate anchors 24a and 24b. However, the cable 40 can be movably connected to each of the intermediate anchors 24a and 24b in any desired manner or combination of manners.

Additionally, the cable 40 is adapted to be connected to each of the rotary anchors 30a and 30b so as to also be movable relative thereto. To accomplish this, the illustrated cable 40 includes one or more tooth-engaging portions 41 that are adapted to engage the rotary anchors 30a and 30b of the scoliosis correcting device 20. In the illustrated embodiment, a single tooth-engaging portion 41 is provided on the central portion of the cable 40. The structure of the tooth-engaging portion 41 is illustrated in detail in FIGS. 2 through 7. As shown therein, the tooth-engaging portion 41 of the cable 40 is somewhat enlarged in size (although such is not required) and has a plurality of openings or recesses 42 formed therein. The openings or recesses 42 are adapted to receive the radially outwardly extending teeth 33b provided on the outer circumferential surface of the sprocket 33, as best shown in FIGS. 3 through 6. However, each of the rotary anchors 30a and 30b can be movably connected to the cable 40 in any desired manner or combination of manners.

The cable 40 may be formed from any desired material, such as titanium, stainless steel, cobalt-chrome, or any other suitable biomaterial. Preferably, the cable 40 is formed from a material that is relatively flexible, which allows bending about the rotary anchors 30a and 30b but is relatively inextensible, for a purpose that will be explained below.

The installation and operation of the scoliosis correcting device 20 will now be described. The scoliosis correcting device 20 is installed by initially securing the fixed anchors 21a and 21b, the intermediate anchors 24a and 24b, and the rotary anchors 30a and 30b to the desired vertebrae 10, 11, and 12 of the spine, as shown in FIG. 1. Such securement of these anchors 21a and 21b, 24a and 24b, and 30a and 30b can be accomplished using any conventional methodology. Preferably, these anchors 21a and 21b, 24a and 24b, and 30a and 30b are inserted in a percutaneous manner through small skin incisions or similar minimally invasive surgical techniques.

Next, the cable 40 is installed on the anchors 21a and 21b, 24a and 24b, and 30a and 30b, as also shown in FIG. 1. This can be accomplished in any desired manner. For the fixed anchors 21a and 21b, the retainers 23a and 23b can be removed from the generally U-shaped yokes 22a and 22b, thereby allowing the portions of the cable 40 to be disposed therein. Thereafter, the retainers 23a and 23b can be re-installed on the generally U-shaped yokes 22a and 22b and fully tightened so as to frictionally engage the portions of the cable 40 extending therethrough. Thus, the cable 40 is immovably connected to each of the fixed anchors 21a and 21b. Similarly, for the intermediate anchors 24a and 24b, the retainers 26a and 26b can be removed from the generally U-shaped yokes 25a and 25b, thereby allowing the portions of the cable 40 to be disposed therein. Thereafter, the retainers 26a and 26b can be re-installed on the generally U-shaped yokes 25a and 25b and partially tightened so as to retain, but not frictionally engage, the portions of the cable 40 extending therethrough. Lastly, for the rotary anchors 30a and 30b, the covers 35 can be removed from the head portions 31, thereby allowing the tooth-engaging portions 41 of the cable 40 to be disposed about the radially outwardly extending teeth 33b provided on the sprocket 33. Thereafter, the covers 35 can be re-installed on the head portions 31 so as to positively retain the cable 40 about the radially outwardly extending teeth 33b provided on the sprocket 33. The flange portions 35a of the covers 35 positively retain the tooth-engaging portions 41 of the cable 40 on the radially outwardly extending teeth 33b provided on the sprocket 33.

In operation, it is known that as a child or adolescent with scoliosis matures, the growth and elongation of the convex side of the spine (the right side of the portion of the spine illustrated in FIG. 1) is typically greater than the growth and elongation of the concave side of the spine (the left side of the portion of the spine illustrated in FIG. 1). Normally, this differential growth characteristic will exacerbate the scoliotic orientation of the vertebrae 10, 11, and 12 illustrated in FIG. 1. However, the scoliosis correcting device 20 takes advantage of this differential growth characteristic to automatically ameliorate the scoliotic orientation of the vertebrae 10, 11, and 12. Additionally, this automatic amelioration of the scoliotic orientation of the vertebrae 10, 11, and 12 occurs without the need for undesirable repeated surgical procedures.

To accomplish this, a first portion of the cable 40 is secured to the fixed anchor 21a provided on the concave side of the spine, and a second portion of the cable 40 is secured to the fixed anchor 21b provided on the convex side of the spine, as described above. Thus, the length of the cable 40 that extends from the fixed anchor 21a provided on the concave side of the spine to the fixed anchor 21b provided on the convex side of the spine is fixed when the scoliosis correcting device 20 is installed on the vertebrae 10, 11, and 12. However, as also discussed above, the cable 40 is engaged by the intermediate anchors 24a and 24b and the rotary anchors 30a and 30b for movement relative thereto. Thus, the cable 40 spans across the vertebrae 10, 11, and 12 from the convex side of the spine to the concave side thereof.

Figure 8:
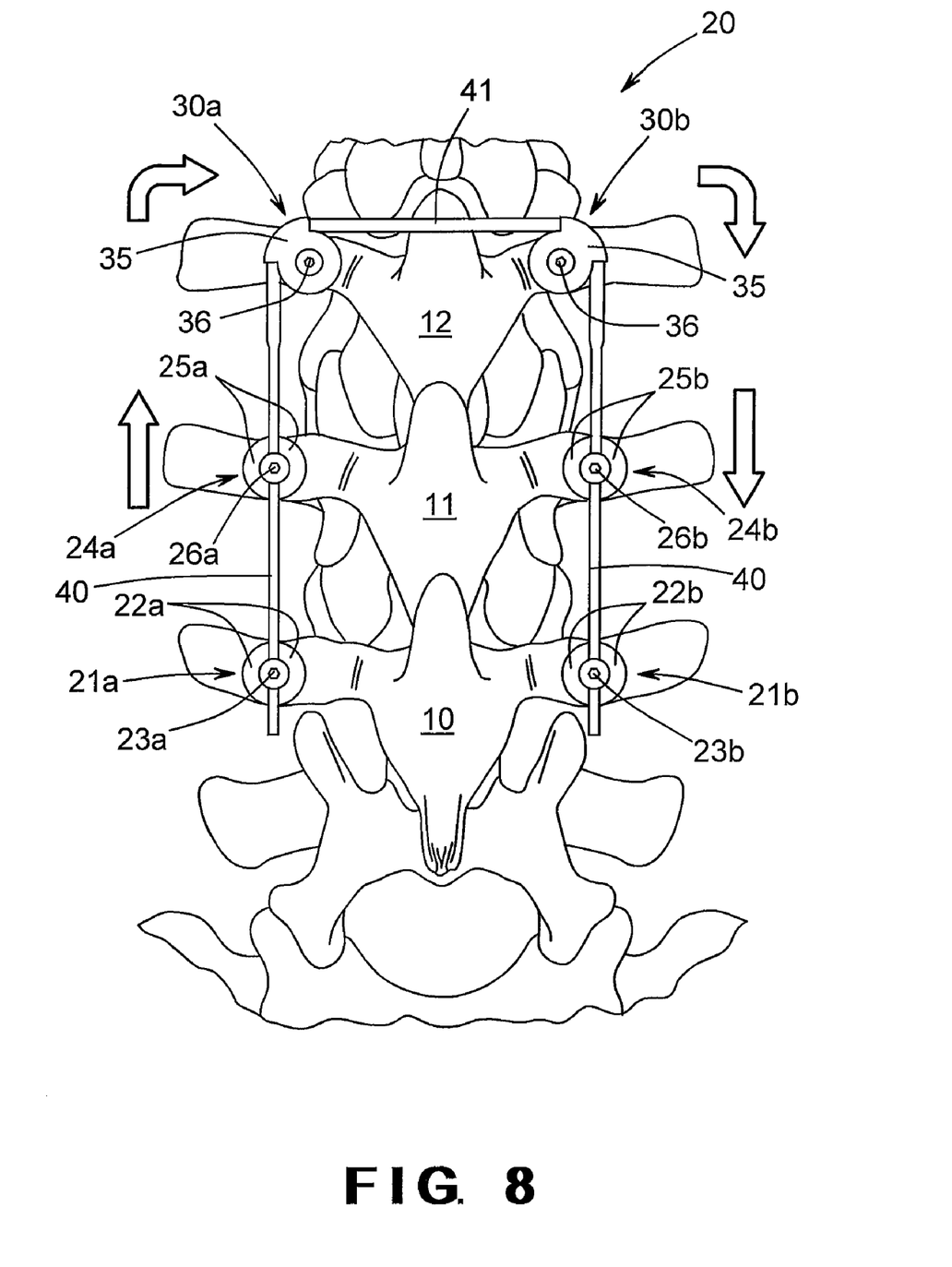
FIG. 8 is a schematic elevational view similar to FIG. 1, wherein the vertebrae of the spine are shown in a subsequent corrected orientation.

As growth and elongation of the convex side of the spine occurs, the cable 40 on the convex side exerts a corrective force (illustrated by the arrows in FIG. 8) on the fixed anchor 21a provided on the concave side of the vertebra 10. The exertion of this corrective force is permitted to occur because of the rotary anchors 30a and 30b, which together function to transfer the corrective force from the convex side of the spine to the concave side thereof. Consequently, the corrective force is exerted on the concave side of the spine and, in particular, the concave side of the vertebra 10. As a result, the three vertebrae 10, 11, and 12 are automatically moved to a corrected orientation illustrated in FIG. 8, wherein the left sides of the vertebrae 10, 11, and 12 are spaced apart from one another by approximately the same distances as the right sides thereof. Therefore, the scoliotic condition of the vertebrae 10, 11, and 12 illustrated in FIG. 1 is significantly corrected.

As discussed above, it is desirable (but not required) that the sprocket 33 be supported on the head portion 31 of the rotatory anchor 30*a* for unidirectional rotational movement relative thereto, i.e., for movement relative to the head portion 31 in one rotational direction but not in the opposite rotational direction. This is done to insure that once the cable 40 has effected some corrective movement of the vertebrae 10, 11, and 12 (as indicated by the arrows in FIG. 8), regressive movement in the opposite direction (i.e., back toward the original position of the vertebrae 10, 11, and 12 illustrated in FIG. 1) cannot occur.

Figure 9:
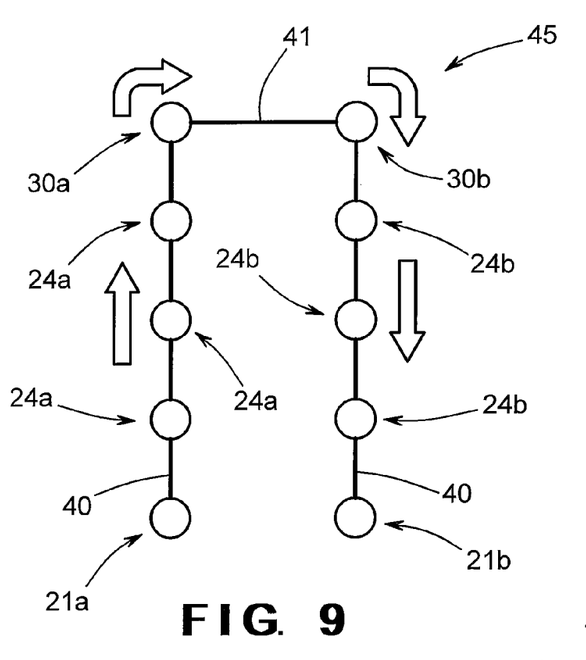
FIG. 9 is a schematic elevational view of a second embodiment of a scoliosis correcting device in accordance with this invention.

FIG. 9 is a schematic elevational view of a second embodiment of a scoliosis correcting device, indicated generally at 45, in accordance with this invention. The second embodiment of the scoliosis correcting device 45 is, in large measure, similar to the first embodiment of the scoliosis correcting device 30 described above, and like reference numbers are used to indicate similar components. In the second embodiment of the scoliosis correcting device 45, however, multiple pairs of intermediate anchors 24*a* and 24*b* are provided on each of a plurality of vertebrae (not shown) located within the intermediate portion of the scoliotic portion of the spine. In the illustrated embodiment, three of such pairs of intermediate anchors 24*a* and 24*b* are provided on each of three intermediate vertebrae of the spine. However, the intermediate anchors 24*a* and 24*b* may be provided on a greater or lesser number of pairs of intermediate vertebrae of the spine as desired. The operation of the second embodiment of the scoliosis correcting device 45 is otherwise the same as the first embodiment of the scoliosis correcting device 30 described above.

Figure 10:
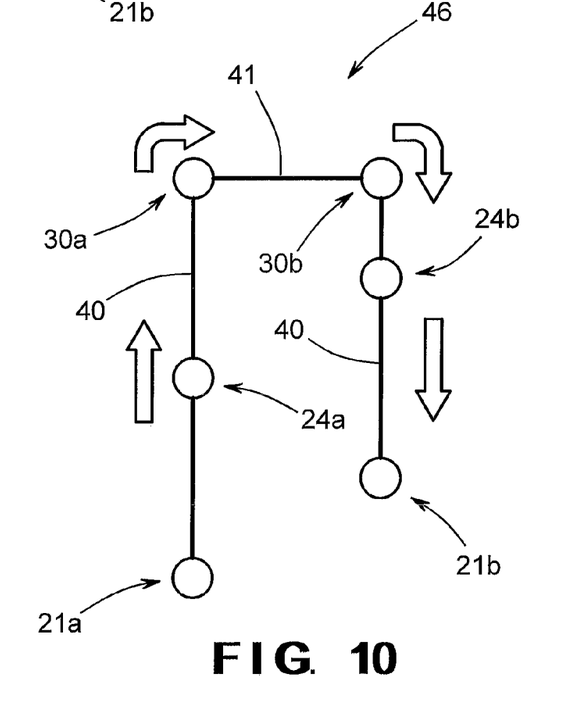
FIG. 10 is a schematic elevational view of a third embodiment of a scoliosis correcting device in accordance with this invention.

FIG. 10 is a schematic elevational view of a third embodiment of a scoliosis correcting device, indicated generally at 46, in accordance with this invention. The third embodiment of the scoliosis correcting device 46 is, in large measure, similar to the first embodiment of the scoliosis correcting device 30 described above, and like reference numbers are used to indicate similar components. In the third embodiment of the scoliosis correcting device 46, however, the intermediate anchors 24*a* and 24*b* are provided on alternating ones and alternating sides of the vertebrae (not shown) located within the intermediate portion of the scoliotic portion of the spine. In the illustrated embodiment, two of such intermediate anchors 24*a* and 24*b* are provided on alternative sides of alternative ones of the intermediate vertebrae of the spine. However, the intermediate anchors 24*a* and 24*b* may be provided on a greater or lesser number of intermediate vertebrae of the spine as desired and in any desired arrangement. The operation of the third embodiment of the scoliosis correcting device 46 is otherwise the same as the first embodiment of the scoliosis correcting device 30 described above.

Figure 11:
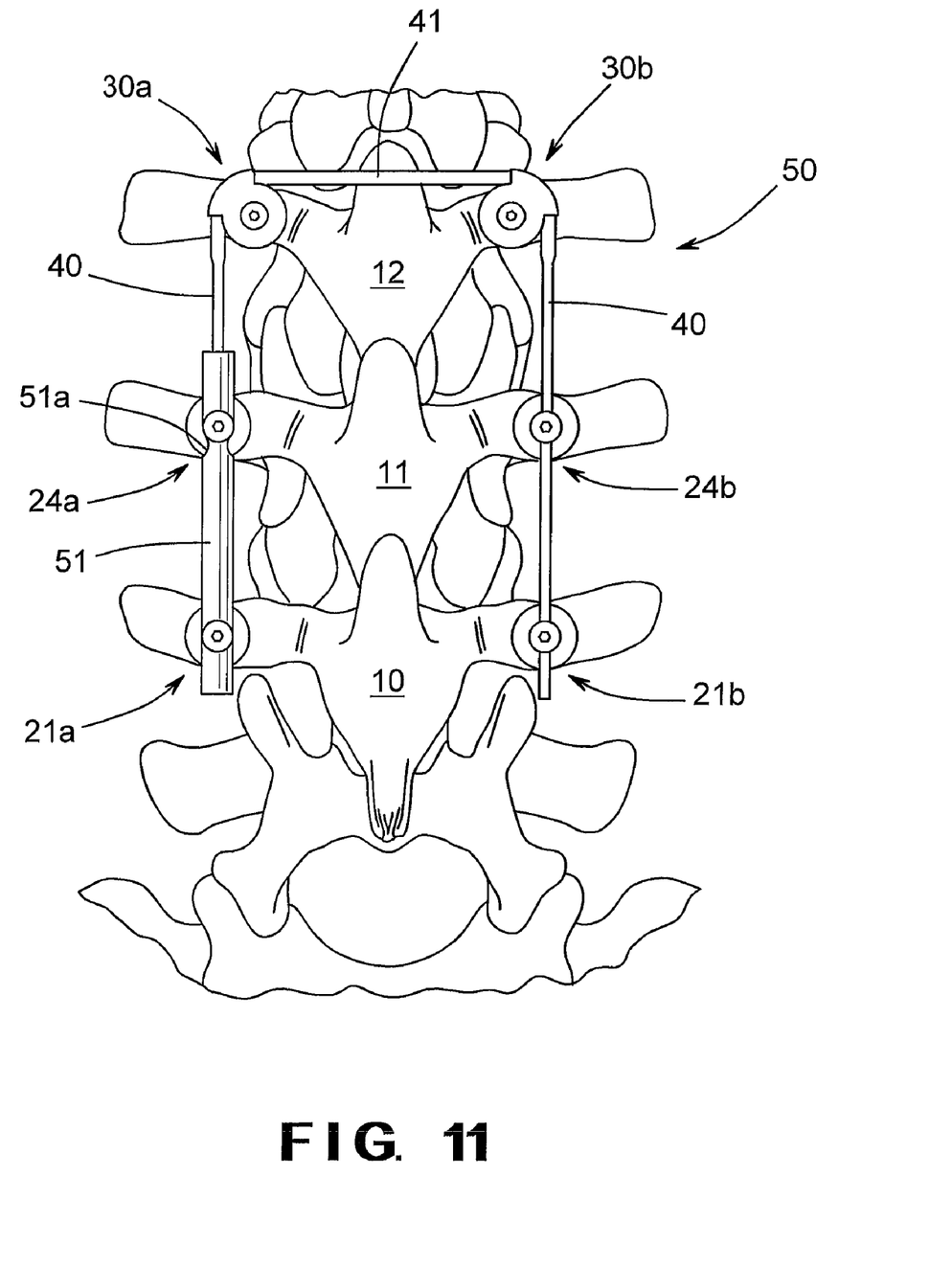
FIG. 11 is a schematic elevational view of three vertebrae of a portion of a spine having a fourth embodiment of a scoliosis correcting device in accordance with this invention secured thereto, wherein the vertebrae of the spine are shown in a subsequent corrected orientation.

FIG. 11 is a schematic elevational view of the three vertebrae 10, 11, and 12 having a fourth embodiment of a scoliosis correcting device, indicated generally at 50, in accordance with this invention secured thereto. The fourth embodiment of the scoliosis correcting device 50 is, in large measure, similar to the first embodiment of the scoliosis correcting device 30 described above, and like reference numbers are used to indicate similar components. In the fourth embodiment of the scoliosis correcting device 50, however, a rigid member 51 is provided between two of the adjacent vertebrae, such as the first and second vertebrae 10 and 11. The illustrated rigid member 51 is generally hollow and cylindrical in shape. However, the rigid member 51 may be formed having any desired shape. In the illustrated embodiment, the rigid member 51 is secured to the fixed anchor 21*a* provided on the concave side of the spine. The rigid member 51 can be secured to the fixed anchor 21*a* in any desired manner. For example, the rigid member 51 may be provided with an aperture (not shown) through which the fixed anchor 21*a* extends. However, the rigid member 51 is connected to the intermediate anchor 24*a* for movement relative thereto. Thus, the distance between the fixed anchor 21*a* and the intermediate anchor 24*a* can change as growth and elongation of the convex side of the spine occurs, as described above. If desired, a mechanism can be provided for limiting the movement of the intermediate anchor 24*a* relative to the rigid member 51. In the illustrated embodiment, this movement limiting mechanism is a crimped area 51*a* that is provided in the rigid member 51. The crimped area 51*a* permits the intermediate anchor 24*a* to move away from the fixed anchor 21*a* (such as will occur as the scoliotic condition is corrected), but prevents the intermediate anchor 24*a* from moving back closer to the fixed anchor 21*a*. Thus, the crimped area 51*a* defines a predetermined minimum distance between the fixed anchor 21*a* and the intermediate anchor 24*a*. The cable 40 extends through the interior of the illustrated hollow rigid member 51 and is secured to the fixed anchor 21*a* and to the intermediate anchor 24*a* in the same manner as described above. The operation of the fourth embodiment of the scoliosis correcting device 50 is otherwise the same as the first embodiment of the scoliosis correcting device 30 described above.

Figure 12:
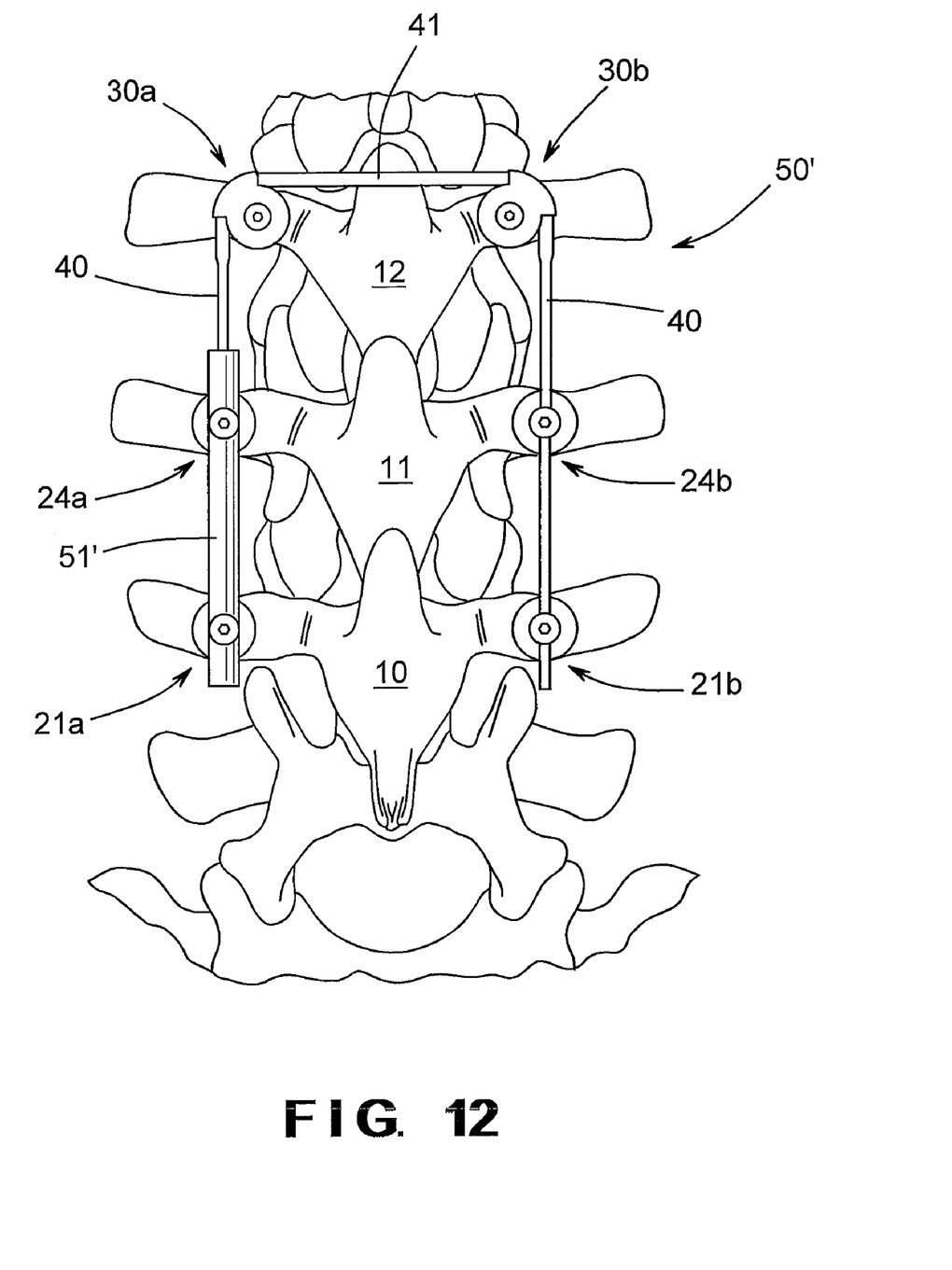
FIG. 12 is a schematic elevational view of three vertebrae of a portion of a spine having a fifth embodiment of a scoliosis correcting device in accordance with this invention secured thereto, wherein the vertebrae of the spine are shown in a subsequent corrected orientation.

FIG. 12 is a schematic elevational view of the three vertebrae 10, 11, and 12 having a fifth embodiment of a scoliosis correcting device, indicated generally at 50', in accordance with this invention secured thereto. The fifth embodiment of the scoliosis correcting device 50' is, in large measure, similar to the fourth embodiment of the scoliosis correcting device 50 described above, and like reference numbers are used to indicate similar components. In the fifth embodiment of the scoliosis correcting device 50', however, a rigid member 51' is provided between two of the adjacent vertebrae 10 and 11. The illustrated rigid member 51' is generally hollow and cylindrical in shape. However, the rigid member 51' may be formed having any desired shape. In the illustrated embodiment, the rigid member 51' is secured to both the fixed anchor 21*a* and to the intermediate anchor 24*a* provided on the concave side of the spine. The rigid member 51' can be secured to the fixed anchor 21*a* land to the intermediate anchor 24*a* in any desired manner. For example, the rigid member 51' may be provided with respective apertures (not shown) through which the fixed anchor 21*a* and the intermediate anchor 24*a* extend. Regardless, because the rigid member 51' is secured to the fixed anchor 21*a* and to the intermediate anchor 24*a*, the distance between the fixed anchor 21*a* and the intermediate anchor 24*a* is fixed and, therefore, cannot change as growth and elongation of the convex side of the spine occurs, as described above. The cable 40 extends through the interior of the illustrated hollow rigid member 51' and is secured to the fixed anchor 21*a* and to the intermediate anchor 24*a* in the same manner as described above. Thus, except for the fixed distance between the fixed anchor 21*a* and the intermediate anchor 24*a* provided by the hollow rigid member 51, the operation of the fifth embodiment of the scoliosis correcting device 50' is otherwise the same as the forth embodiment of the scoliosis correcting device 50 described above.

Figures 13, 14:
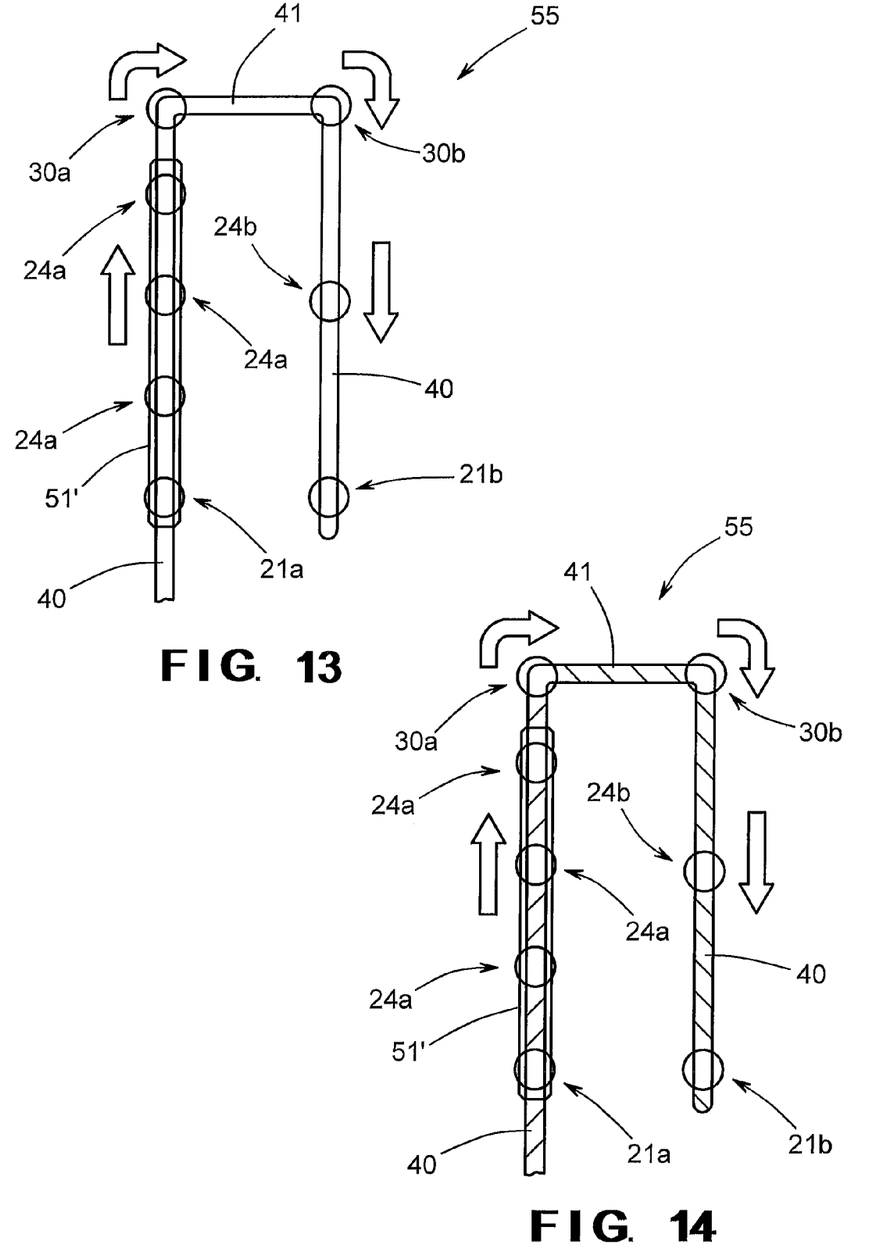
FIG. 13 is a schematic elevational view of a sixth embodiment of a scoliosis correcting device in accordance with this invention.
FIG. 14 is a schematic elevational view in cross section of the sixth embodiment of a scoliosis correcting device illustrated in FIG. 13.

FIGS. 13 and 14 are schematic views of a sixth embodiment of a scoliosis correcting device, indicated generally at 55, in accordance with this invention. The sixth embodiment of the scoliosis correcting device 55 is, in large measure, similar to the fourth embodiment of the scoliosis correcting device 50 described above, and like reference numbers are used to indicate similar components. In the sixth embodiment of the scoliosis correcting device 55, however, multiple intermediate anchors 24a are provided on a plurality of vertebrae (not shown) located within the intermediate portion of the scoliotic portion of the spine. In the illustrated embodiment, three of such intermediate anchors 24a are provided on three intermediate vertebrae of the spine. However, the intermediate anchors 24a may be provided on a greater or lesser number of intermediate vertebrae of the spine as desired. The rigid member 51' can be either movable or fixedly connected to the intermediate anchors 24a provided on the intermediate vertebrae of the spine as desired. The operation of the sixth embodiment of the scoliosis correcting device 55 is otherwise the same as the fourth embodiment of the scoliosis correcting device 50 described above.

Figure 15:
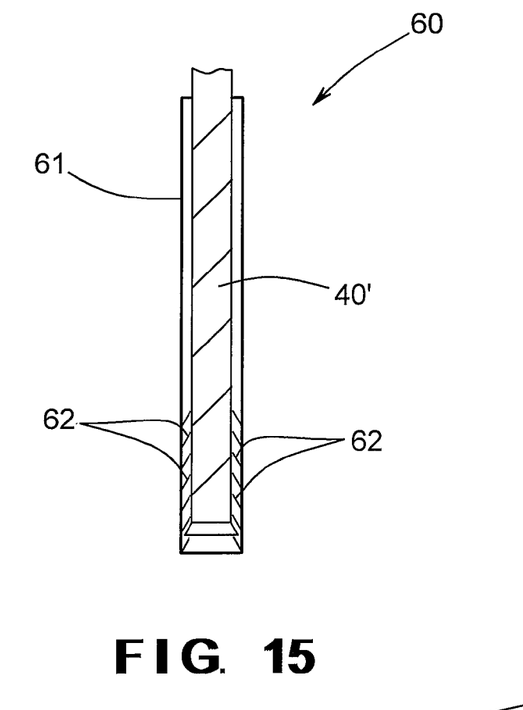
FIG. 15 is a schematic sectional elevational view of a portion of a seventh embodiment of a scoliosis correcting device in accordance with this invention, located in a retracted position.
Figure 16:
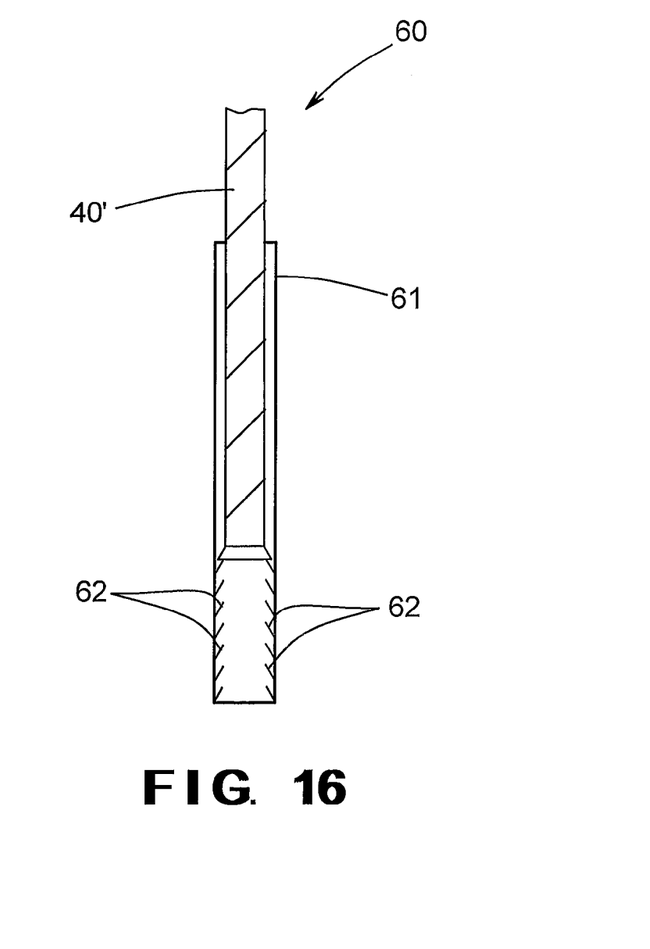
FIG. 16 is a schematic sectional elevational view of the portion of the seventh embodiment of the scoliosis correcting device illustrated in FIG. 15, located in an extended position.

FIGS. 15 and 16 illustrate a portion of a seventh embodiment of a scoliosis correcting device, indicated generally at 60, in accordance with this invention. The seventh embodiment of the scoliosis correcting device 60 is, in large measure, similar to the fourth embodiment of the scoliosis correcting device 50 described above, and like reference numbers are used to indicate similar components. In the seventh embodiment of the scoliosis correcting device 60, however, no crimped area 51a is provided in the rigid member 51 to permit the intermediate anchor 24a to move away from the fixed anchor 21a, but prevent the intermediate anchor 24a from moving back toward to the fixed anchor 21a. Rather, the mechanism for limiting the movement of the intermediate anchor 24a relative to the fixed anchor 21a is an alternative rigid member 61 that includes an internal one-way movement structure 62. In the illustrated embodiment, the one-way movement structure 62 is a series of ratchet-like structures that engage a solid end portion 40' attached to or formed integrally with the cable 40. As clearly shown in FIGS. 14 and 15, the ratchet-like structures 62 permit the end portion 40' of the cable 40 to be extended from the rigid member 61 (such as will occur as the scoliotic condition is corrected), but prevent the end portion 40' of the cable 40 from being retracted back within the rigid member 61. The operation of the seventh embodiment of the scoliosis correcting device 60 is otherwise the same as the fourth embodiment of the scoliosis correcting device 50 described above.

Figure 17:
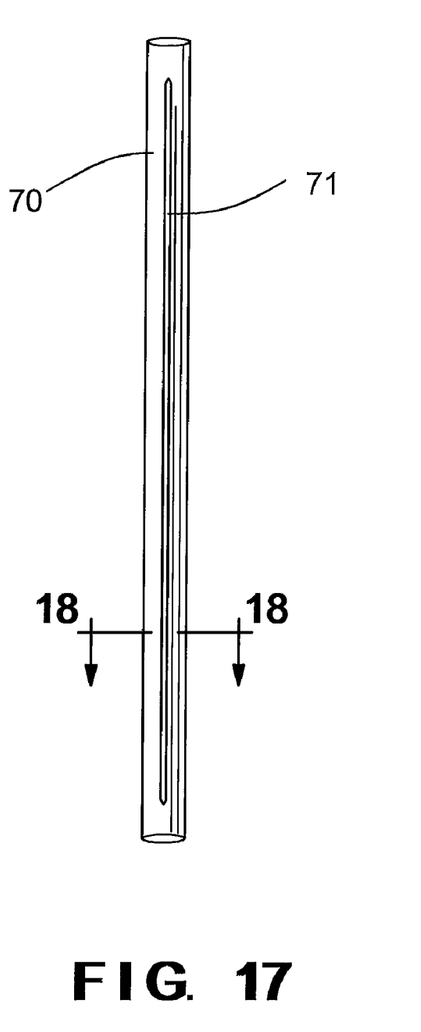
FIG. 17 is a schematic side elevational view of the portion of an alternative embodiment of a rigid member in accordance with this invention.
Figure 18:
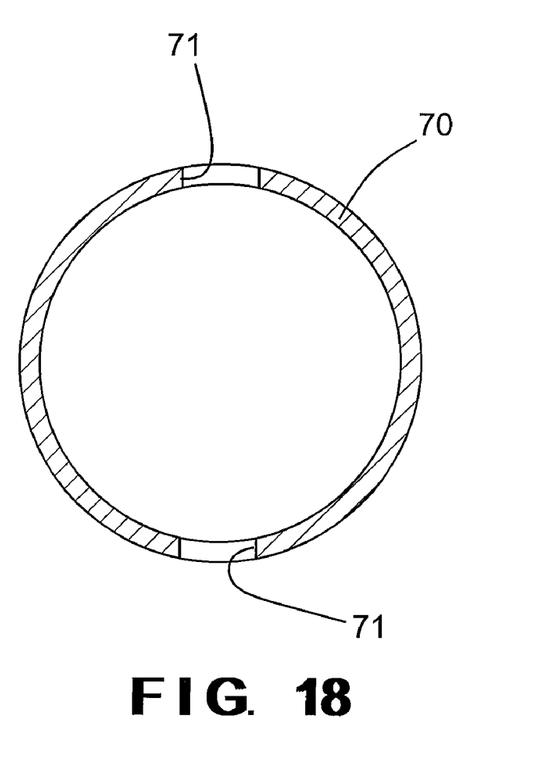
FIG. 18 is a schematic sectional elevational view taken along line 18-18 of FIG. 17.

FIGS. 17 and 18 illustrates an alternative embodiment of a rigid member, indicated generally at 70, in accordance with this invention that can be used in conjunction with any of the scoliosis correcting devices described above. In this embodiment of the rigid member 70, two slots 71 are extend throughout most of the axial length thereof. However, it will be appreciated that a greater or less number of such slots 71 may be provided at any desired location or locations on the rigid member 70. The slots 71 may be provided to facilitate the determination of the position of the cable 40 therein or to assist in positioning the cable 40 at a desired location therein.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A rotatory anchor adapted for use in a scoliosis correcting device comprising:
   a head portion including a sprocket; and
   a shank portion that extends from the head portion and is adapted to be secured to a vertebra of a spine;
   wherein the sprocket is supported on the head portion for unidirectional rotational movement relative thereto, wherein the sprocket is adapted to cooperate with a portion of a scoliosis correcting device.

2. The rotatory anchor defined in claim 1 wherein the head portion includes an outer circumferential surface, and wherein the sprocket includes an inner circumferential surface that is supported on the outer circumferential surface of the head portion for rotational movement relative thereto.

3. The rotatory anchor defined in claim 1 wherein the sprocket has a plurality of radially outwardly extending teeth provided on an outer circumferential surface thereof.

4. The rotatory anchor defined in claim 1 wherein the head portion includes an outer circumferential surface, and wherein the sprocket includes an inner circumferential surface that is supported on the outer circumferential surface of the head portion for unidirectional rotational movement relative thereto.

5. The rotatory anchor defined in claim 4 wherein a recess is provided in the outer circumferential surface of the head portion, and wherein at least one ball bearing is provided within the recess that engages the inner circumferential surface of the sprocket to cause the unidirectional rotational movement.

6. The rotatory anchor defined in claim 4 wherein a plurality of recesses is provided in the outer circumferential surface of the head portion, and wherein at least one ball bearing is provided within each of the recesses that engages the inner circumferential surface of the sprocket to cause the unidirectional rotational movement.

7. A scoliosis correction device comprising:
   a first fixed anchor adapted to be secured to be secured to a vertebra of a spine;
   a second fixed anchor adapted to be secured to be secured to a vertebra of a spine;
   a rotatory anchor including a head portion, a shank portion that extends from the head portion and is adapted to be secured to a vertebra of a spine, and a sprocket that is supported on the head portion for rotational movement relative thereto; and
   a cable extending from the first fixed anchor to the rotatory anchor to the second fixed anchor.

8. The scoliosis correction device defined in claim 7 wherein the head portion includes an outer circumferential surface, and wherein the sprocket includes an inner circumferential surface that is supported on the outer circumferential surface of the head portion for rotational movement relative thereto.

9. The scoliosis correction device defined in claim 7 wherein the sprocket has a plurality of radially outwardly extending teeth provided on an outer circumferential surface thereof.

10. The scoliosis correction device defined in claim 7 wherein the sprocket is supported on the head portion for unidirectional rotational movement relative thereto.

11. The scoliosis correction device defined in claim 7 wherein the head portion includes an outer circumferential surface, and wherein the sprocket includes an inner circumferential surface that is supported on the outer circumferential surface of the head portion for unidirectional rotational movement relative thereto.

12. The scoliosis correction device defined in claim 11 wherein a recess is provided in the outer circumferential surface of the head portion, and wherein at least one ball bearing is provided within the recess that engages the inner circumferential surface of the sprocket to cause the unidirectional rotational movement.

13. The scoliosis correction device defined in claim 11 wherein a plurality of recesses is provided in the outer circumferential surface of the head portion, and wherein at least one ball bearing is provided within each of the recesses that engages the inner circumferential surface of the sprocket to cause the unidirectional rotational movement.

14. The scoliosis correction device defined in claim 7 further including an intermediate anchor that is adapted to be secured to a vertebra of a spine, wherein the cable extends from the first fixed anchor to the intermediate anchor to the rotatory anchor to the second fixed anchor.

15. The scoliosis correction device defined in claim 14 further including a rigid member that extends between the first fixed anchor and the intermediate anchor.

16. The scoliosis correction device defined in claim 7 wherein the cable is fixed in position relative to the first fixed anchor and the second fixed anchor and is movable relative to the intermediate anchor.

17. The scoliosis correction device defined in claim 7 wherein the rotatory anchor is a first rotatory anchor, and further including a second rotatory anchor including a head portion, a shank portion that extends from the head portion and is adapted to be secured to a vertebra of a spine, and a sprocket that is supported on the head portion for rotational movement relative thereto, wherein the cable extends from the first fixed anchor to the first rotatory anchor to the second rotatory anchor to the second fixed anchor.

18. The scoliosis correction device defined in claim 17 further including an intermediate anchor that is adapted to be secured to a vertebra of a spine, wherein the cable extends from the first fixed anchor to the intermediate anchor to the first rotatory anchor to the second rotatory anchor to the second fixed anchor.

19. A rotatory anchor adapted for use in a scoliosis correcting device comprising:
a head portion including a sprocket; and
a shank portion that extends from the head portion and is externally threaded so as to be adapted to be secured to a vertebra of a spine;
wherein the sprocket is supported on the head portion for rotational movement relative thereto, wherein the sprocket is adapted to cooperate with a portion of a scoliosis correcting device.

* * * * *

UNITED STATES PATENT AND TRADEMARK OFFICE
CERTIFICATE OF CORRECTION

PATENT NO. : 8,394,124 B2
APPLICATION NO. : 12/818258
DATED : March 12, 2013
INVENTOR(S) : Ashok Biyani It is certified that error appears in the above-identified patent and that said Letters Patent is hereby corrected as shown below:

In the Claims:

Column 12, Line 38, Claim 7, delete second occurrence of "to be secured".

Column 12, Line 40, Claim 7, delete second occurrence of "to be secured".

Signed and Sealed this
Seventh Day of May, 2013

Teresa Stanek Rea
*Acting Director of the United States Patent and Trademark Office*